United States Patent [19]

Posner

[11] Patent Number: 5,672,624
[45] Date of Patent: Sep. 30, 1997

[54] ENDOPEROXIDES USEFUL AS ANTIPARASITIC AGENTS

[75] Inventor: Gary H. Posner, Baltimore, Md.

[73] Assignee: The Johns Hopkins University, Baltimore, Md.

[21] Appl. No.: 562,275

[22] Filed: Nov. 22, 1995

[51] Int. Cl.⁶ .................. A61K 31/335; A61K 31/075; C07D 321/12; C07D 323/00
[52] U.S. Cl. .................. 514/450; 514/714; 514/895; 549/347; 549/350
[58] Field of Search .................. 514/714, 895, 514/450; 549/347, 350

[56] References Cited

U.S. PATENT DOCUMENTS

| | | | |
|---|---|---|---|
| 4,977,174 | 12/1990 | Stein et al. | 514/382 |
| 5,057,501 | 10/1991 | Thanfeldt | 514/53 |
| 5,578,637 | 11/1996 | Lai et al. | 514/450 |

*Primary Examiner*—C. Warren Ivy
*Assistant Examiner*—Raymond Covington
*Attorney, Agent, or Firm*—Cushman darby & Cushman IP Group of Pillsbury Madison & Sutro

[57] ABSTRACT

The present invention relates to novel biologically-active organic peroxides and to novel uses of both known and new organic peroxides. More specifically, this invention details organic endoperoxides having antiparasitic activity, methods for their preparation and methods for treating malaria and cerebral toxoplasmic encephalitis with the organic endoperoxides.

4 Claims, No Drawings

ENDOPEROXIDES USEFUL AS ANTIPARASITIC AGENTS

The invention described and claimed herein was made in part under a grant from the National Institutes of Health, NIH-AI-34885. The Government has certain rights in the invention.

BACKGROUND OF THE INVENTION

1. Field of the Invention

The present invention relates to novel biologically-active organic peroxides and to novel uses of both known and new organic peroxides. More specifically, this invention details organic endoperoxides having antiparasitic activity, methods for their preparation and methods for treating malaria and cerebral toxoplasmic encephalitis with the organic endoperoxides.

2. Description of the Related Art

The trioxane drug artemisinin is an active anti-malarial constituent of the herb *Artemisia annua L., Compositae*. The herb has been known in China for almost 2000 years. Artemisinin was first isolated in 1972 and shown to be a sesquiterpene lactone with a peroxide moiety (1). The molecular configuration was first reported in 1983 (2) and is shown in the following formula:

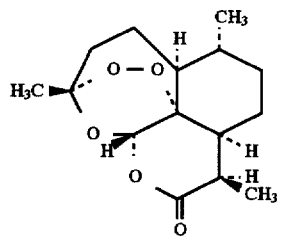

Several investigators have reported on the anti-malarial activity of artemisinin (3–5). Several reviews of the chemistry, pharmacology and clinical applications of artemisinin have been reported (6–8).

We have used our understanding of molecular mechanisms of action to design and synthesize a series of structurally simple endoperoxides patterned after artemisinin, some of which have previously been reported (9–11). Biological evaluation of these synthetic organic peroxides has surprisingly shown some of them to be potent antiparasitic agents with considerable activity against not only malaria but also against cerebral toxoplasmic encephalitis caused by *Toxoplasma gondii*.

SUMMARY OF THE INVENTION

The present invention is for saturated bicyclo (3,2,2) endoperoxide compounds of the formula:

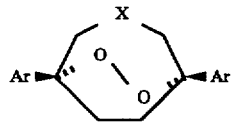

wherein Ar is phenyl and X is selected from the group consisting of:

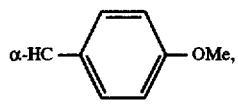

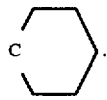

$C(CH_3)_2$, and

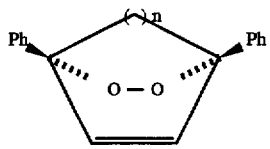

The present invention is also for unsaturated bicyclic endoperoxide compounds of the formula:

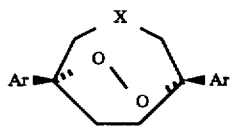

wherein n is 4.

The present invention also relates to a method for treating malaria comprising the step of administering an organic endoperoxide to an individual afflicted with malaria, wherein the organic peroxide is selected from the group consisting of:

a) a compound of the formula:

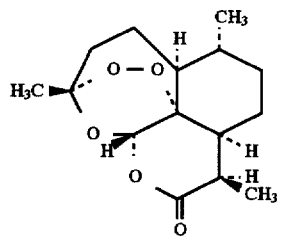

wherein Ar is selected from the group consisting of Ph and p-MeOPh and X is selected from the group consisting of:

$CH_2$,

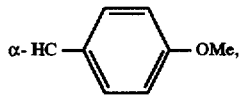

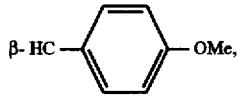

$SO_2$, $C(CH_3)_2$, and

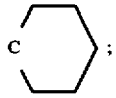

b) a compound of the formula:

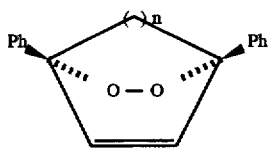

wherein n is 1, 2, 3 or 4; and c) a compound of the formula:

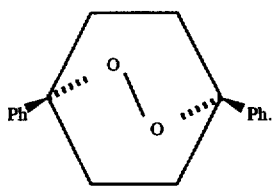

The present invention also relates to a method for treating cerebral toxoplasmic encephalitis comprising the step of administering an organic endoperoxide to an individual afflicted with cerebral toxoplasmic encephalitis, wherein the organic peroxide is selected from the group consisting of:

a) a compound of the formula:

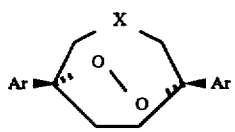

wherein Ar is selected from the group consisting of Ph and p-MeOPh and X is selected from the group consisting of:

$CH_2$,

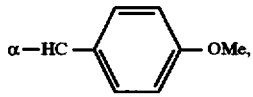

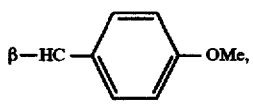

$SO_2$, $C(CH_3)_2$, and

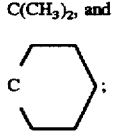

b) a compound of the formula:

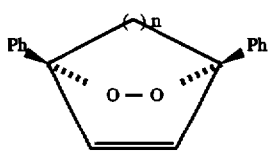

wherein n is 1, 2, 3 or 4; and c) a compound of the formula:

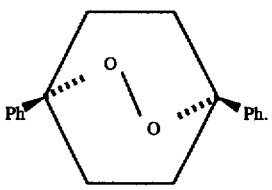

DETAILED DESCRIPTION OF THE INVENTION

As mention above, the present invention relates to novel organic endoperoxides having antiparasitic activity, methods for their preparation and methods for treating malaria and cerebral toxoplasmic encephalitis with the organic endoperoxides. A detailed description for the methods of preparation of the synthetic organic endoperoxides and for the testing of the biological activity of the compounds follows:

1. Preparation of the Endoperoxides

The organic endoperoxides of the present invention were prepared as follows. Compounds of the formula:

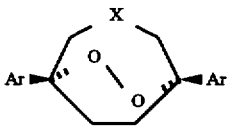

wherein Ar is selected from the group consisting of Ph and p-MeOPh and X is $CH_2$ were prepared according to the method of Takahashi et al. (11).

The compound of the formula:

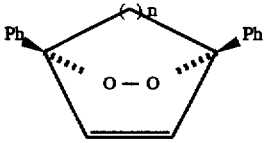

wherein n is 1 was prepared according to the method of Kuhn (12).

The compound of the formula:

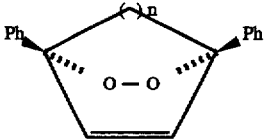

wherein n is 2 was prepared according to the method of Schenck et al. (13).

The compound of the formula:

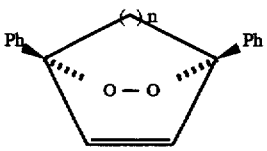

wherein n is 3 was prepared according to the method of Rigaudy et al. (14).

Bicyclo[3.2.2]C-5-p-methoxyphenyl diphenyl peroxides of the formula:

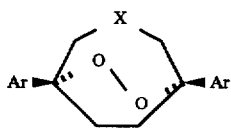

wherein Ar is Ph and X is

or

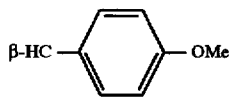

were prepared according to the following procedures.

General.

Tetrahydrofuran (THF) and diethyl ether (Et$_2$O) were distilled from benzophenone ketyl prior to use. Methylene chloride, (CH$_2$Cl$_2$) and triethylamine (NEt$_3$) were distilled from calcium hydride prior to use. Commercially available anhydrous solvents were used in other instances. Unless otherwise noted, all reagents were purchased from Aldrich Chemical Co. (Milwaukee, Wis.) and were used as received without further purification. FT-IR spectra were recorded using a Perkin-Elmer Model 1600 FT-IR spectrophotometer. The $^1$H and $^{13}$C NMR spectra were recorded on a Varian XL-400 spectrometer operating 400 MHz and 100 MHz, respectively. Chemical shifts are reported in parts per million (ppm, δ) downfield from tetramethylsilane. Splitting patterns are described as singlet (s), doublet (d), triplet (t), quartet (q), multiplet (m), etc. Low resolution mass spectra (LRMS) and High resolution mass spectra (HRMS) were obtained on VG Instruments 70-S spectrometer run at 70 eV for electronic ionization (EI) or with ammonia (NH$_3$) as a carrier for chemical ionization (CI). High performance liquid chromatography (HPLC) was performed by a Rainin HPLX gradient system. Column chromatography was performed by Silica 60 (70–230 mesh, Merck) or florisil (200 mesh, Aldrich). The reaction vessels were usually oven-dried overnight. Reaction yields are not optimized.

Scheme I.
The synthesis of bicyclo[3.2.2] C-5-p-methoxyphenyl diphenyl peroxides 2

PEROXIDES 2α AND 2β.

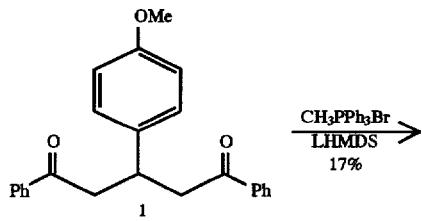

-continued
Scheme I.
The synthesis of bicyclo[3.2.2] C-5-p-methoxyphenyl diphenyl peroxides 2

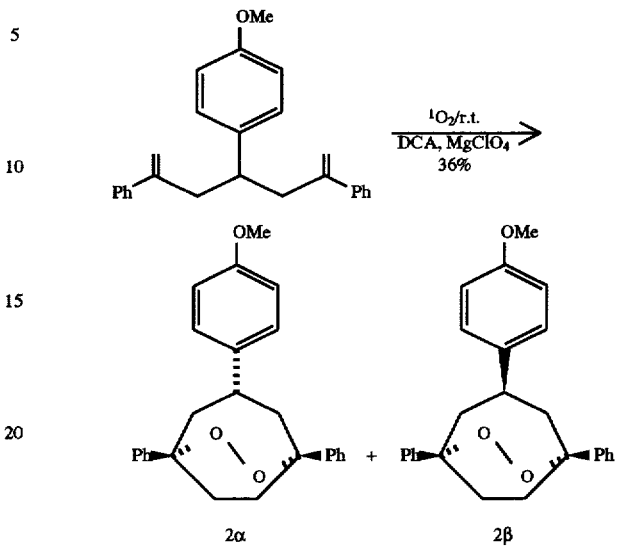

Step 1: An oven-dried round bottom flask charged with commercial pre-dried methyltriphenylphosphonium bromide (3.99 g, 11.2 mmol) and dry THF (20 ml) was cooled down to −78° C. under argon atmosphere. To the solution was added lithium bis(trimethylsilyl)amide (LHMDS; 1M in THF, 14 ml, 14.0 mmol) over 3 min. The resultant yellow ylide solution was stirred at −78° C. for 10 min, then allowed to warm to room temperature and stirred for 1.5 hr. After cooling down again to −78° C., the reaction mixture was treated with commercial diketone (448 mg, 1.25 mmol) in dry THF (5 mL) via a cannula over 5 min. After being stirred at −78° C. for 20 min, the reaction mixture was slowly warmed up to room temperature over 4 hr, stirred for 26 hr at room temperature and then cooled down to 0° C., quenched with warer (10 ml) at 0° C. and diluted with ether (10 ml). The organic layer was separated, and the aqueous layer was extracted twice with ether (10 ml×2). The combined organic layer was washed with brine solution (20 ml), and dried over anhydrous magnesium sulfate, filtered, and concentrated under reduced pressure to yield a crude product which was purified by silica gel column chromatography using 1:99 ethyl acetate: hexane to afford the corresponding diene (74.5 mg, 17%) as colorless oil.

Step 2: An oven-dried 125 ml three necked round-bottomed flask, fitted with magnetic stir-bar, gas inlet and outlet, was charged with the diene (93.4 mg, 0.26 mmol), dicyanoanthracene (DCA; 3 mg), and anhydrous acetonitrile (25 ml). Dry oxygen (flow rate: ca. 1 ml/s) was bubbled to this solution at room temperature for 30 min. Magnesium perchlorate (590 mg, 2.64 mmol) was added into the flask, and oxygen was continuously bubbled through the reaction mixture at room temperature for 2 hr under UV irradiation using a medium-pressure mercury lamp as UV source. The resultant solution was then diluted with water (20 ml) and ether (10 ml), the organic layer was separated, and the aqueous layer was extracted twice with ether (10 ml×2). The combined organic layer was washed with brine solution (20 ml), and dried over anhydrous magnesium sulfate, filtered, and concentrated under reduced pressure to yield a crude product which was purified by silica gel column chromatography using 1:99 ethyl acetate:hexane to afford the corresponding peroxides 2 (36.6 mg, 36%), which were separated by HPLC to give 2α (16.3 mg) and 2β (19.2 mg) both as white solids.

2α: m.p.: 163–164° C.; FTIR (CHCL₃, cm⁻¹): 2954, 2931, 2872, 2849, 1611, 1511, 1490, 1467, 1443, 1302, 1249, 1210, 1179, 1032; ¹H NMR (CDCl₃, 400 MHz) δ 7.46–7.42 (m, 4 H), 7.36–7.31 (m, 4 H), 7.26–7.23 (m, 4 H), 6.86–6.83 (m, 2 H), 3.95 (m, 1 H), 3.78 (s, 3 H), 2.70–2.64 (m, 2 H), 2.53–2.38 (m, 6 H); ¹³C NMR (CDCl₃, 100 MHz) δ 158.05, 146.89, 137.81, 128.32, 128.21, 127.17, 124.26, 113.93, 80.70, 55.29, 49.81, 38.46, 32.99; LRMS (EI, 70 eV, rel intensity) 386 (M, 1), 354 (M-O₂, 1), 239 (18) 237 (11), 159 (11), 143 (13), 129 (13), 121 (14), 104 (100), 91 (20), 77 (40);

HRMS calc. for C₂₆H₂₆O₃ (M⁺) 386.1882, found 386.1878;

2β: m.p.: 202°–203° C.; FTIR (CHCl₃, cm⁻¹): 3008, 2955, 2932, 2838, 1611, 1513, 1494, 1447, 1462, 1373, 1304, 1248, 1215, 1178, 1037; ₁H NMR (CDCl₃, 400 MHz) δ 7.46–7.41 (m, 4 H), 7.32–7.27 (m, 4 H), 7.23–7.19 (m, 4 H), 6.81–6.78 (m, 2 H), 3.73 (s, 3 H), 3.44 (m, 1 H), 2.60–2.53 (m, 4 H), 2.41–2.32 (m, 4 H); ₁₃C NMR (CDCl₃, 100 MHz) δ 150.89, 145.88, 137.27, 128.28, 128.24, 124.36, 113.92, 82.27, 55.27, 49.14, 39.23, 29.29; LRMS (EI, 70 eV, rel intensity) 386 (M, 2), 354 (M-O₂, 1), 239 (53), 161 (10), 134 (29), 121(11), 105 (100), 91 (13), 77 (38); HRMS calc. for C₂₆H₂₆O₃ (M₊) 386.1882, found 386.1885.

Comparable compounds wherein X is

SO₂,

C(CH₃)₂, or

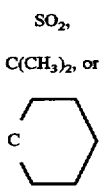

were prepared by comparable procedures.

The compound of the formula:

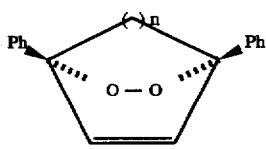

wherein n is 4 was prepared according to the following procedure. 1,4-Diphenyl-1,3-cyclooctadiene (281 mg, 1.08 mmol), prepared according to the method of Cope et al. (15), was dissolved in dry methylene chloride. To this solution, methylene blue (5 mg) was added. The blue solution was then cooled to −78° C. Dry oxygen was slowly bubbled into the reaction solution under UV irradiation with a medium pressure mercury lamp for 5 hr while the reaction was allowed to warm to room temperature. The reaction mixture was concentrated to give a residue which was subjected to silica gel column chromatography (hexanes/ethyl acetate, 95/5) and further purified by HPLC to give a white solid 26.5 mg, yield 8.4%, m.p. 80.5°–81° C. ¹H NMR (400 MHz, CDCl₃) δ 7.51(4H, ddd, J=7.2, 2.0, 1.6 Hz), 7.36(4H, m), 7.28(2H, tt, J=7.6, 2.0 Hz), 6.35(2H, s), 2.38–2.30(2H, m), 2.15–1.93(6H, m); ¹³C NMR (100 MHz, CDCl₃) δ 143.353 (2C), 130.920(2C), 128.371(4C), 127.522(2C), 125.299 (4C), 82.113(2C), 39.738(2C), 25.469(2C); LRMS Calc. for C₂₀H₂₀O₂, 292 (m⁺), found, 292.

2. Biological Activity of the Endoperoxides a. Antimalarial Activity

The protozoan *Plasmodium falciparum* is a causative agent of malaria, the single most critical infectious disease of mankind. The antimalarial activity of the endoperoxides was determined according to the method of Desjardins et al. (16) as modified by Milhous et al. (17). Briefly, the antimalarial activity of the endoperoxides was tested in a tritiated-hypoxanthine incorporation assay by determining the concentration of the test compound needed to inhibit 50% of the replication of *Plasmodium falciparum* (IC₅₀) in human red blood cells.

b. Activity Against *Toxoplasma Gondii*

*Toxoplasma gondii* is the causative agent of cerebral toxoplasmic encephalitis, an AIDS-related opportunistic infection. The biological activity of the endoperoxide JHU 2886 of the present invention was measured against *Toxoplasma gondii* cultured in L929 cells.

More specifically, the cytotoxicity of synthetic organic endoperoxide JHU 2886 was tested in L929 cells by measuring the viability and replication of exposed cells. The cytotoxicity of the compound to the cultured cells was measured using the MTT assay (Promega kit), according to the procedure of Carmichael et al. (18). MTT is an abbreviation for [3-(4,5-dimethylthiazol-2-yl)-2,5-dephenyltetrazolium bromide].

The inhibitory activity of the synthetic organic endoperoxide was tested by measuring the intracellular replication of *T. gondii* in infected L929 cells. The inhibition of the intracellular replication of *T. gondii* was determined using the uracil incorporation assay (20).

The results from these tests are shown in Table 1. More specifically, Table 1 shows the effect of a compound of the formula:

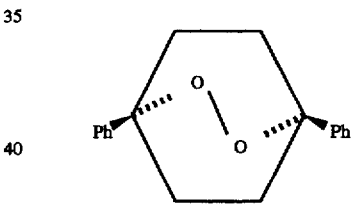

on the viability and replication of L929 cells and on the intracellular replication of *T. gondii*. This compound is referred to as JHU 2886 in Table 1. In this experiment atovaquone and artemisinin were used as positive controls. Atovaquone is a broad-spectrum anti-infective drug having antimalarial and antitoxoplasmosis activity (19).

As shown in Table 1, there was little toxicity seen after 24, 48 and 72 hours in L929 cells exposed to concentrations of JHU 2886 as high as 10 μM. There was some toxicity seen at concentrations of 50 μM. There was significant antiparasitic activity seen at 24 and 48 hours at all concentrations of JHU 2886 tested. There was significant activity seen at 72 hours for concentrations of 1 μM and above.

Table 2 shows the structures of several organic endoperoxides of the present invention. The upper section shows seven saturated bicyclo (3,2,2) endoperoxides. The first two compounds are known while the following five are being disclosed for the first time. The far right column shows the concentration of the compound needed to inhibit 50% of the replication of *Plasmodium falciparum* (IC₅₀) in human red blood cells, as determined in the tritiated-hypoxanthine incorporation assay.

The bottom section of Table 2 shows the structure of a known unsaturated endoperoxide. This compound is identical to the unsaturated seven carbon ring compound in Table 3. The $IC_{50}$ for this compound is give as 150 nM in both Table 2 and Table 3. The bottom section of Table 2 also reveals the $IC_{50}$ for the naturally-occurring artemisinin.

Table 3 shows the structures of several unsaturated organic endoperoxides of the present invention. The first three compounds are known while the following compound is being disclosed for the first time. Again, the far right column shows the concentration of the compound needed to inhibit 50% of the replication of *Plasmodium falciparum* ($IC_{50}$) in human red blood cells, as determined in the tritiated-hypoxanthine incorporation assay.

While the invention has been described in connection with what is presently considered to be the most practical and preferred embodiments, it is to be understood that the invention is not to be limited to the disclosed embodiments, but on the contrary is intended to cover various modifications and equivalent arrangements included within the spirit and scope of the appended claims, including other anti-infective uses.

The following scientific articles and references have been cited throughout this application and the entire contents of each article or reference is hereby incorporated by reference.

SCIENTIFIC ARTICLES

1. Jing-Ming, J., et al., *Acta Chim. Sinica* 37:129 (1979).
2. Schmid, G., et al., *J. Am. Chem. Soc.* 105:624 (1983).
3. Qinghaosu Antimalaria Coordinating Research Group, *Chinese Med. J.* 92:811 (1979).
4. Jiang, J.-B., et al., *Lancet* 2:285 (1982).
5. Bruce-Chwatt, L. J., *Brit. Med. J.* 284:767 (1982).
6. Luo, X. D., et al., *Med. Res. Rev.* 7:29–52 (1987).
7. Klayman, D. L., *Science* 228:1049–1054 (1985).
8. Koch, H., *Pharm. Int.* 2:184–185 (1981).
9. Miyashi, T., et al., *J. Am. Chem. Soc.* 110:3676–3677 (1988).
10. Miyashi, T., et al., *Pure & Appl. Chem.* 62:1531–1538 (1990).
11. Takahashi, Y., et al., *Tetrahedron Letters* 35:3953–3956 (1994).
12. Kuhn, H. J., *Diplomarbeit*, Univ. Gottingen (1959).
13. Schenck, G. O., et al., *Naturwissenschaften* 41:374 (1954).
14. Rigaudy, J., et al., *Tetrahedron Letters* pp. 95–99 (1961).
15. Cope, A. C., et al., *J. Am. Chem. Soc.* 77:4939–4940 (1955).
16. Desjardins, R. E., et al., *Antimicrob. Agents Chemother.* 16:710–718 (1979).
17. Milhous, W. K., et al., *Antimicrob. Agents Chemother.* 27:525–530 (1985).
18. Carmichael, J., et al., *Cancer Res.* 936–942 (1987).
19. Hudson, A. T., *Parasitology Today* 9:66–68 (1993).
20. Fraser, D. C., et al., *Biochem. Biophys. Res. Comm.* 135:886–893 (1986).

TABLE 1

JUSTIFICATION OF SOME COMPOUNDS BASED ON THE VIABILITY AND REPLICATION OF L929 CELLS AND ON THE INTRACELLULAR REPLICATION OF *T. gondii*

| Drug Experiment[1] | Dose μM | 24 Hours | | | | 48 Hours | | | | 72 Hours | | | |
|---|---|---|---|---|---|---|---|---|---|---|---|---|---|
| | | Mean | S.D. | % of control | Score[2] | Mean | S.D. | % of control | Score[2] | Mean | S.D. | % of control | Score[2] |
| Atovaquone Toxicity | 0.0 | 0.113 | 0.008 | | | 0.213 | 0.009 | | | 0.438 | 0.014 | | |
| | 0.1 | 0.095 | 0.006 | 15.63 | 1 | 0.214 | 0.002 | 0.00 | 0 | 0.473 | 0.021 | 0.00 | 0 |
| | 1.0 | 0.093 | 0.003 | 17.40 | 1 | 0.211 | 0.008 | 1.09 | 1 | 0.464 | 0.033 | 0.00 | 0 |
| | 10.0 | 0.092 | 0.002 | 18.29 | 1 | 0.204 | 0.013 | 4.53 | 1 | 0.456 | 0.023 | 0.00 | 0 |
| | 50.0 | 0.089 | 0.010 | 21.24 | 2 | 0.106 | 0.009 | 50.16 | 3 | 0.161 | 0.005 | 63.24 | 3 |
| Atovaquone Activity | 0.0 | 14351 | 3588 | | | 17225 | 946 | | | 7234 | 1994 | | |
| | 0.1 | 3096 | 373 | 78.43 | 4 | 6865 | 512 | 60.15 | 3 | 2940 | 677 | 59.36 | 3 |
| | 1.0 | 693 | 98 | 95.17 | 5 | 729 | 90 | 95.77 | 5 | 1272 | 117 | 82.42 | 4 |
| | 10.0 | 612 | 67 | 95.74 | 5 | 399 | 56 | 97.68 | 5 | 446 | 136 | 93.84 | 5 |
| | 50.0 | 1042 | 121 | 92.74 | 5 | 236 | 35 | 98.63 | 5 | 230 | 405 | 96.82 | 5 |
| Artemisinin Toxicity | 0.0 | 0.113 | 0.008 | | | 0.213 | 0.009 | | | 0.438 | 0.014 | | |
| | 0.1 | 0.103 | 0.007 | 8.56 | 1 | 0.213 | 0.009 | 0.00 | 0 | 0.460 | 0.015 | 0.00 | 0 |
| | 1.0 | 0.101 | 0.004 | 10.32 | 1 | 0.205 | 0.007 | 3.75 | 1 | 0.394 | 0.013 | 9.97 | 1 |
| | 10.0 | 0.104 | 0.003 | 7.67 | 1 | 0.195 | 0.009 | 8.44 | 1 | 0.354 | 0.014 | 19.18 | 1 |
| | 50.0 | 0.110 | 0.006 | 2.36 | 1 | 0.193 | 0.006 | 9.53 | 1 | 0.348 | 0.006 | 20.55 | 2 |
| Artemisinin Activity | 0.0 | 14351 | 3588 | | | 17225 | 946 | | | 7234 | 1994 | | |
| | 0.1 | 10106 | 2429 | 29.58 | 2 | 15440 | 1999 | 10.36 | 1 | 8253 | 3474 | −14.10 | 0 |
| | 1.0 | 3467 | 1028 | 75.84 | 4 | 6101 | 990 | 64.58 | 3 | 1976 | 1051 | 72.68 | 4 |
| | 10.0 | 3470 | 843 | 74.82 | 4 | 4225 | 327 | 75.47 | 4 | 783 | 388 | 89.17 | 4 |
| | 50.0 | 33322 | 810 | 76.85 | 4 | 4167 | 117 | 75.81 | 4 | 813 | 285 | 88.77 | 4 |
| JHU 2886 Toxicity | 0.0 | 0.129 | 0.005 | | | 0.211 | 0.006 | | | 0.439 | 0.014 | | |
| | 1.0 | 0.129 | 0.005 | 0.26 | 1 | 0.227 | 0.003 | 0.00 | 0 | 0.479 | 0.026 | 0.00 | 0 |
| | 1.0 | 0.133 | 0.005 | 0.00 | 0 | 0.219 | 0.009 | 0.00 | 0 | 0.460 | 0.008 | 0.00 | 0 |
| | 10.0 | 0.130 | 0.005 | 0.00 | 0 | 0.217 | 0.008 | 0.00 | 0 | 0.448 | 0.023 | 0.00 | 0 |
| | 50.0 | 0.089 | 0.005 | 31.19 | 2 | 0.147 | 0.008 | 30.38 | 2 | 0.275 | 0.005 | 37.43 | 2 |
| JHU 2886 Activity | 0.00 | 8782 | 1629 | | | 15819 | 1074 | | | 7166 | 784 | | |
| | 0.1 | 6079 | 91 | 30.78 | 2 | 14841 | 2301 | 6.18 | 1 | 6934 | 1197 | 3.24 | 1 |
| | 1.0 | 2668 | 386 | 69.62 | 3 | 12880 | 1946 | 18.58 | 1 | 6219 | 2202 | 13.21 | 1 |
| | 10.0 | 1967 | 259 | 77.60 | 4 | 4428 | 780 | 72.01 | 4 | 1321 | 244 | 81.57 | 4 |
| | 50.0 | 2104 | 478 | 76.04 | 4 | 1808 | 169 | 88.57 | 4 | 1252 | 217 | 82.53 | 4 |

TABLE 1-continued

JUSTIFICATION OF SOME COMPOUNDS BASED ON THE VIABILITY AND REPLICATION OF L929 CELLS AND ON THE INTRACELLULAR REPLICATION OF *T. gondii*

| | | INHIBITION AT | | | | | | | | | | |
|---|---|---|---|---|---|---|---|---|---|---|---|---|
| | | 24 Hours | | | | 48 Hours | | | | 72 Hours | | |
| Drug Experiment[1] | Dose μM | Mean | S.D. | % of control | Score[2] | Mean | S.D. | % of control | Score[2] | Mean | S.D. | % of control | Score[2] |

[1] The cytotoxicity of each compound for the cultured cells was measured using the MTT assay (Promega kit) and inhibition of the intracellular replication of *T. gondii* was determined using the uracil incorporation assay.
[2] The extent of toxicity or activity (in percent of control) was scored based on the following criterion:
0 = No reduction
1 = ≦20%
2 = >20%–≦40%
3 = >40%–≦70%
4 = >70%–≦90%
5 = >90%

TABLE 2

ANTIMALARIAL ACTIVITY COMPARED TO THE POTENT ANTIMALARIAL ARTEMISININ

| KNOWN | Ar | X | IC$_{50}$ (nM) |
|---|---|---|---|
| Yes | Ph | CH$_2$ | 89 |
| Yes | p-MeOPh | CH$_2$ | 62 |
| | Ph | α-HC—⟨C$_6$H$_4$⟩—OMe | 180 |
| | Ph | β-HC—⟨C$_6$H$_4$⟩—OMe | 410 |
| | Ph | SO$_2$ | >1000 |
| | Ph | C(CH$_3$)$_2$ | >1000 |
| | Ph | C⟨cyclohexyl⟩ | >1000 |
| Yes | 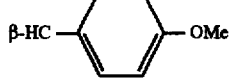 | | 150 |
| Yes | Artemisinin | | 11 |

TABLE 3

ANTIMALARIAL ACTIVITY

| KNOWN | n | Ring Size | IC$_{50}$ (nM) |
|---|---|---|---|
| Yes | 1 | 5 | 650 |
| Yes | 2 | 6 | 150 |
| Yes | 3 | 7 | 150 |
| | 4 | 8 | 410 |

What is claimed is:

1. A saturated bicyclo (3,2,2) endoperoxide compound of the formula:

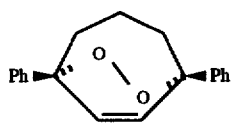

wherein Ar is phenyl and X is selected from the group consisting of:

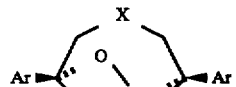 α-HC—⟨ ⟩—OMe,

 β-HC—⟨ ⟩—OMe,

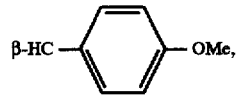 SO$_2$, C(CH$_3$)$_2$, and 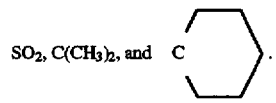 C⟨ ⟩.

2. An unsaturated bicyclic endoperoxide compound of the formula:

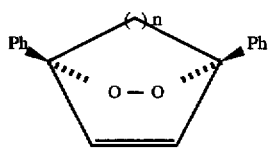

wherein n is 4.

3. A method for treating malaria comprising the step of administering an organic endoperoxide to an individual afflicted with malaria, wherein the organic peroxide is selected from the group consisting of:

a) a compound of the formula:

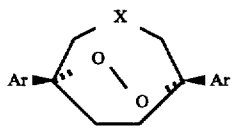

wherein Ar is selected from the group consisting of Ph and p-MeOPh and X is selected from the group consisting of:

$CH_2$,

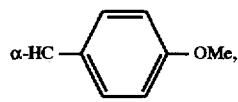

$SO_2$, $C(CH_3)_2$, and

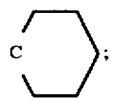;

b) a compound of the formula:

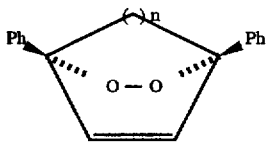

wherein n is 1, 2, 3 or 4; and
c) a compound of the formula:

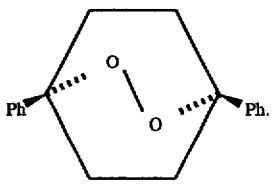

4. A method for treating cerebral toxoplasmic encephalitis comprising the step of administering an organic endoperoxide to an individual afflicted with cerebral toxoplasmic encephalitis, wherein the organic peroxide is selected from the group consisting of:

a) a compound of the formula:

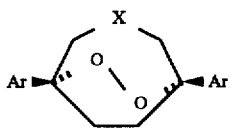

wherein Ar is selected from the group consisting of Ph and p-MeOPh and X is selected from the group consisting of:

$CH_2$,

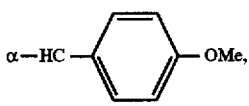

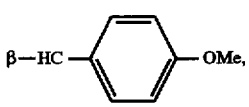

$SO_2$, $C(CH_3)_2$, and

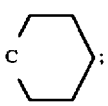;

b) a compound of the formula:

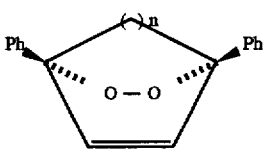

wherein n is 1, 2, 3 or 4; and
c) a compound of the formula:

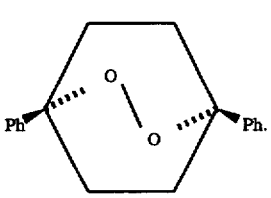

* * * * *